United States Patent
Hynes

(10) Patent No.: US 7,473,269 B1
(45) Date of Patent: Jan. 6, 2009

(54) SPINAL FIXATION SYSTEM AND RELATED METHODS

(75) Inventor: Richard A. Hynes, Melbourne, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 418 days.

(21) Appl. No.: 11/132,972

(22) Filed: May 19, 2005

Related U.S. Application Data

(62) Division of application No. 10/099,797, filed on Mar. 15, 2002, now Pat. No. 7,220,262.

(60) Provisional application No. 60/276,706, filed on Mar. 16, 2001.

(51) Int. Cl.
*A61B 17/88* (2006.01)
*A61B 17/70* (2006.01)

(52) U.S. Cl. ................... 606/279; 606/250

(58) Field of Classification Search ............ 606/70, 606/71, 69, 72, 73, 60, 61, 53, 279, 250, 606/276, 264, 278, 265
See application file for complete search history.

(56) References Cited

U.S. PATENT DOCUMENTS

| | | | |
|---|---|---|---|
| 4,003,376 A | 1/1977 | McKay et al. | |
| 4,369,769 A | 1/1983 | Edwards | |
| 4,662,365 A | 5/1987 | Gotzen et al. | |
| 4,697,582 A | 10/1987 | William | |
| 5,254,118 A | 10/1993 | Mirkovic | |
| 5,261,912 A | 11/1993 | Frigg | |
| 5,387,212 A * | 2/1995 | Yuan et al. ............ | 606/61 |
| 5,437,669 A * | 8/1995 | Yuan et al. ............ | 606/61 |
| 5,437,671 A | 8/1995 | Lozier et al. | |
| 5,466,238 A | 11/1995 | Lin | |
| 5,470,333 A * | 11/1995 | Ray ..................... | 606/61 |
| 5,474,551 A | 12/1995 | Finn et al. | |
| 5,486,174 A | 1/1996 | Fournet-Fayard et al. | |
| 5,507,747 A | 4/1996 | Yuan et al. | |
| 5,514,132 A | 5/1996 | Csernatony et al. | |
| 5,531,745 A | 7/1996 | Ray | |
| 5,531,747 A | 7/1996 | Ray | |
| 5,591,165 A | 1/1997 | Jackson | |
| 5,628,740 A | 5/1997 | Mullane | |
| 5,667,506 A * | 9/1997 | Sutterlin ............... | 606/61 |

(Continued)

FOREIGN PATENT DOCUMENTS

| | | |
|---|---|---|
| EP | 0 465 158 B1 | 1/1997 |
| FR | 2 624 720 | 6/1989 |
| WO | WO 01/54597 | 8/2002 |

*Primary Examiner*—Pedro Philogene
(74) *Attorney, Agent, or Firm*—Krieg DeVault

(57) ABSTRACT

Pedicle screws are secured in two columns, one along each side of the spine. Cross support rods have ends connected to pedicle screw heads. A longitudinally extending rod is supported on the cross supports and recessed in the cavity created by removal of portions of spinous processes, providing a reduced profile of the installed construct. Several types of cross supports are shown such as: arms from the screws inward to rings or yokes connecting the longitudinal rod; cross rods with ends connected to the screws and having centrally-located yokes for the longitudinal rod; cross rods with articulating longitudinal rod portions fixed or swiveled to them. These cross rods may have end portions angled posterior toward anterior to accommodate lateral positioned pedicle screws, but shorter cross rods without angled end portions enable medialized pedicle screw orientation.

34 Claims, 10 Drawing Sheets

U.S. PATENT DOCUMENTS

| | | | |
|---|---|---|---|
| 5,688,275 A | 11/1997 | Koros et al. | |
| 5,702,392 A | 12/1997 | Wu et al. | |
| 5,741,255 A | 4/1998 | Krag et al. | |
| 5,876,403 A | 3/1999 | Shitoto | |
| 6,053,917 A | 4/2000 | Sherman et al. | |
| 6,063,089 A | 5/2000 | Errico et al. | |
| 6,113,601 A | 9/2000 | Tatar | |
| 6,139,548 A | 10/2000 | Errico | |
| 6,146,383 A | 11/2000 | Studer et al. | |
| 6,187,005 B1 | 2/2001 | Brace et al. | |
| 6,224,597 B1 | 5/2001 | Coker | |
| 6,231,575 B1 | 5/2001 | Krag | |
| 6,261,288 B1 | 7/2001 | Jackson | |
| 6,296,644 B1 * | 10/2001 | Saurat et al. | 606/61 |

* cited by examiner

SPINAL FIXATION SYSTEM AND RELATED METHODS

CROSS REFERENCE TO RELATED APPLICATIONS

The present invention is a divisional of application Ser. No. 10/099,797, filed on Mar. 15, 2002, now U.S. Pat. No. 7,220, 262, which claims the benefit of priority of U.S. Provisional Application No. 60/276,706, filed Mar. 16, 2001.

FIELD OF THE INVENTION

The present invention relates to medical devices, and, more particularly, to spinal fixation systems and related methods.

BACKGROUND OF THE INVENTION

Spinal fixation systems may be used to correct and stabilize the position of vertebral segments within a patient's spine. Such correction may be necessary as a result of accidents, degenerative diseases, etc. Typical spine fixation systems in use today include pedicle screws attached to the posterior of a patient's vertebrae in a vertical column along either one or both sides of the spine. A rod is connected to the heads of each pedicle screw in a column to provide support for the spine. Examples of such prior art devices may be seen in U.S. Pat. No. 5,741,255 entitled "Spinal Column Retaining Apparatus" to Krag et al. and U.S. Pat. No. 6,187,005 entitled "Variable Angle Spinal Fixation System" to Brace et al.

Unfortunately, when the above prior art systems are inserted in a patient, the pedicle screws are typically positioned such that the head of each pedicle screw angles outward away from the center of the spine (i.e., in a lateral orientation). Because of this screw angle and the fact that the support rods are mounted at about the same height as the pedicle screw heads, there is a significant amount of trauma to the back muscles when this system is installed. This, in turn, leads to a significant amount of pain after the surgery as well as a long recovery time.

Another spinal fixation system is disclosed in U.S. Pat. No. 5,628,740 entitled "Articulating Toggle Bolt Bone Screw" to Mullane. This spinal fixation system is designed for anterior attachment to a patient's spine and includes two columns of screws on either side of the spine with a single support rod therebetween attached to the screws by clamps, as may be seen in FIG. 5 of the patent. However, while such anterior spinal fixation systems may not cause as severe trauma to back muscles (since they are installed on the opposing side of the spine from the back muscles), it may not be possible to install such devices at certain positions on the spine.

Another limitation of the above systems is that their support rods are typically formed as a unitary piece. Even though such support rods typically have some degree of flexibility, they may not be able to accommodate spines that require correction in multiple directions.

SUMMARY OF THE INVENTION

The invention involves apparatus and method for minimizing the height of profile of spinal implants employed for correcting and stabilizing the position of vertebral segments within a patient's spine. Fasteners are secured in two columns, one on each side of the center of the spine. Cross members are connected to the fasteners and support a spinal rod in space provided by removal of portions of spinous processes involved in the treatment of the patient. In some embodiments, the spinal rod is a one-piece item, and in other embodiments it is a multi-piece assembly with cross supports fixed to longitudinal portions at certain locations and cross supports swiveled to longitudinal portions at other locations. The spinal rod also has portions longitudinally slidable for selectively increasing or decreasing spacing between cross supports. Rotatable or swivel joints are provided according to other features of the invention to enable relative rotation between cross supports about axes of spinal rod portions connecting such cross supports.

BRIEF DESCRIPTION OF THE DRAWINGS

FIG. 2A is a fragmentary view showing a yoke-type pivoting end on the connector arm instead of the ring-type in FIG. 2.

DETAILED DESCRIPTION OF THE ILLUSTRATED EMBODIMENTS

Figure 1:
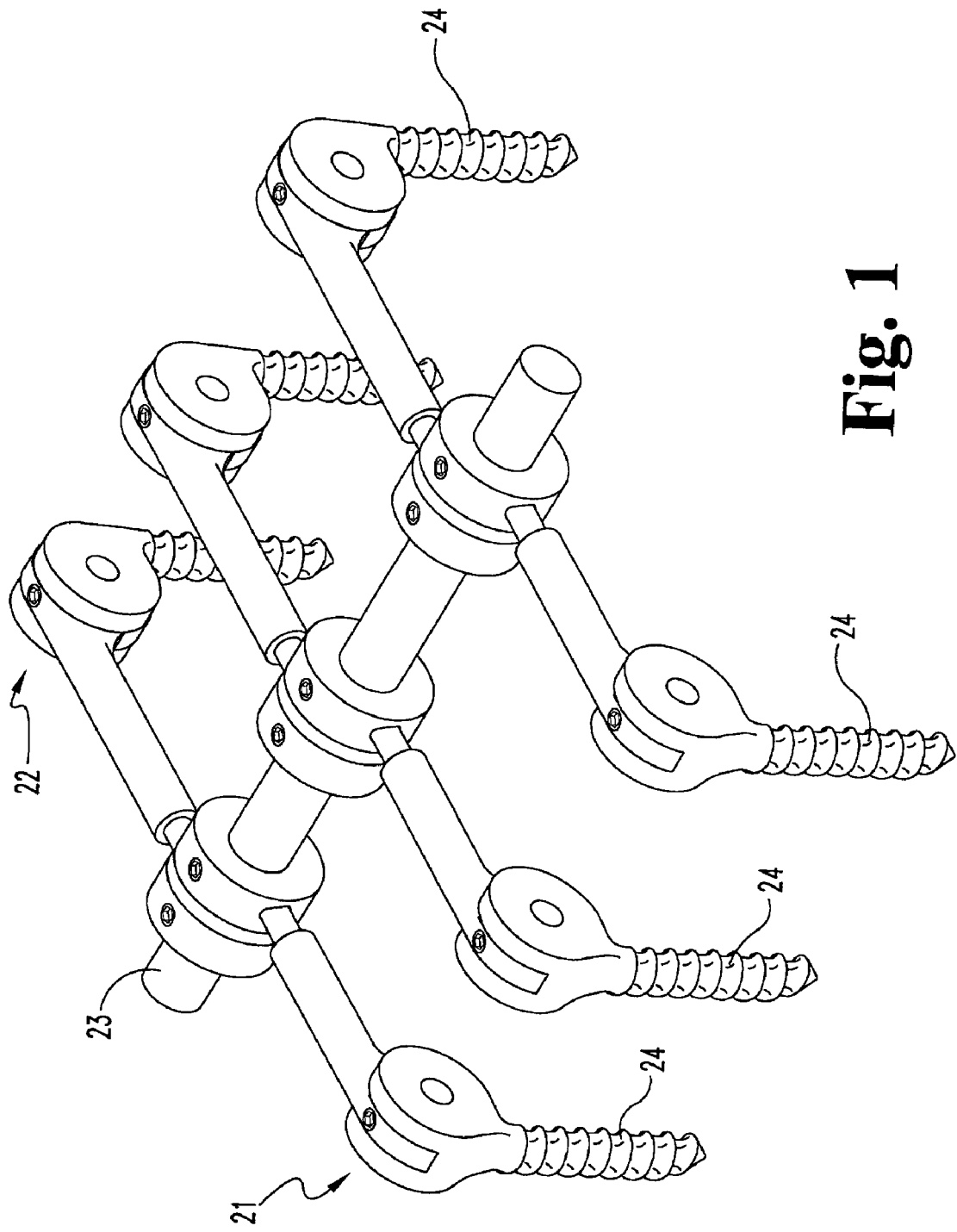
FIG. 1 is a perspective view of one embodiment of apparatus according to the present invention.
Figure 2:
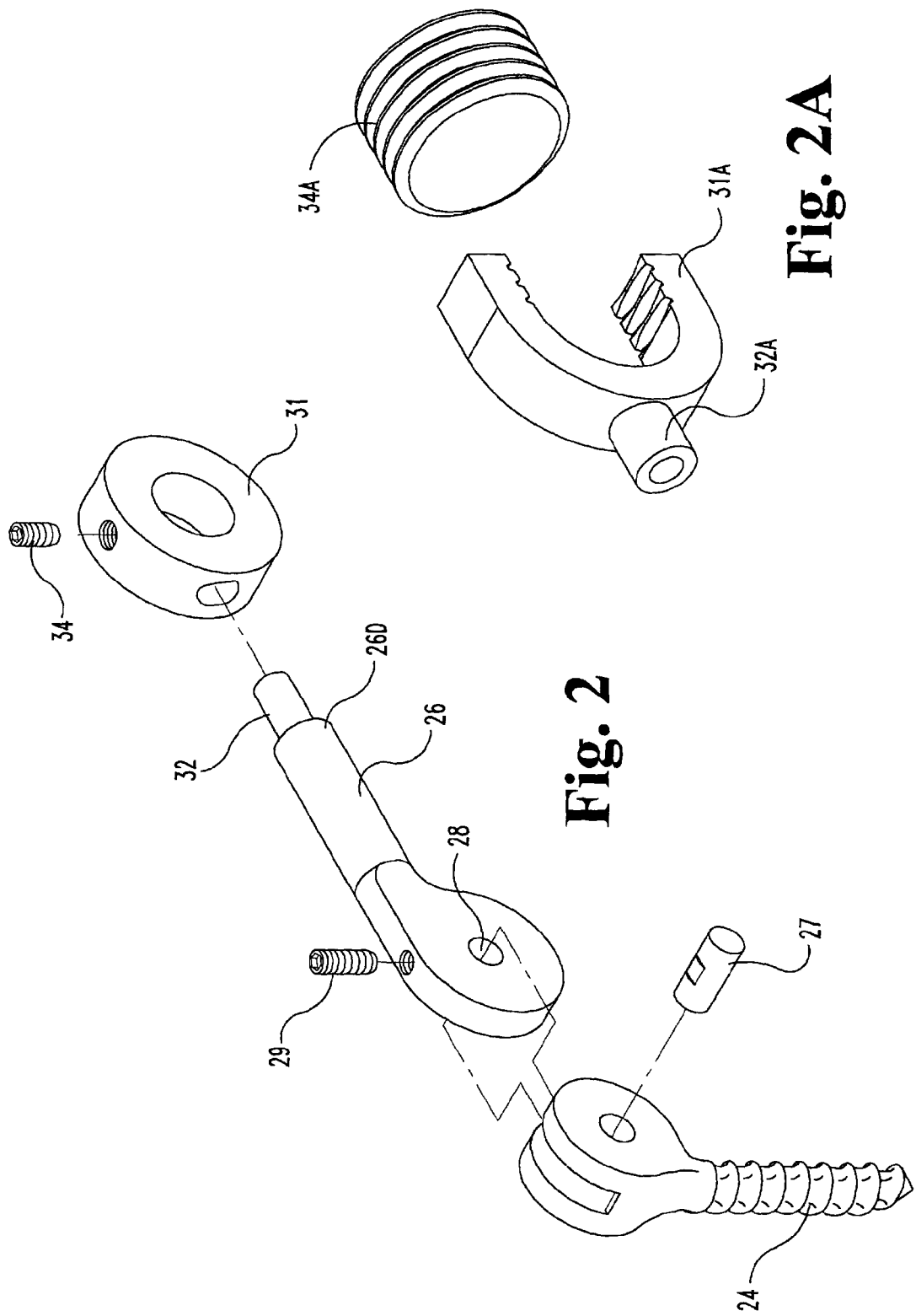
FIG. 2 is an exploded view of one of the combinations of pedicle screw, connector arm and ring assembly of the embodiment of FIG. 1.

Turning now to FIGS. 1-2, one embodiment of a spinal fixation system according to the present invention includes two columns 21, 22 of pedicle screws along each side of a patient's spine and a single support rod 23 positioned between the two columns (i.e., substantially in the center of the spine) and connected to each of the pedicle screws. An example of the connection is shown in the exploded view of FIG. 2 where the pedicle screw 24 has a yoke at the top receiving a proximal end of connector arm 26 retained in the yoke by hinge pin 27, received through aperture 28 in the arm and fixed there by locking screw 29. At the distal end 26D of the arm 26, a ring 31 is connected by multi-axial hinge at 32 and through which the rod 23 is received as shown in FIG. 1 and secured in place by a locking screw 34. FIG. 2A is an example in which a multi-axial screw head 31A on stem 32A with locking screw 34A is substituted for ring 31 of FIGS. 1 and 2. Screw head and stem are of the Medtronic Sofamor Danek, Inc. (MSD) M-8 type mentioned below, but without stem threads.

Figure 4:
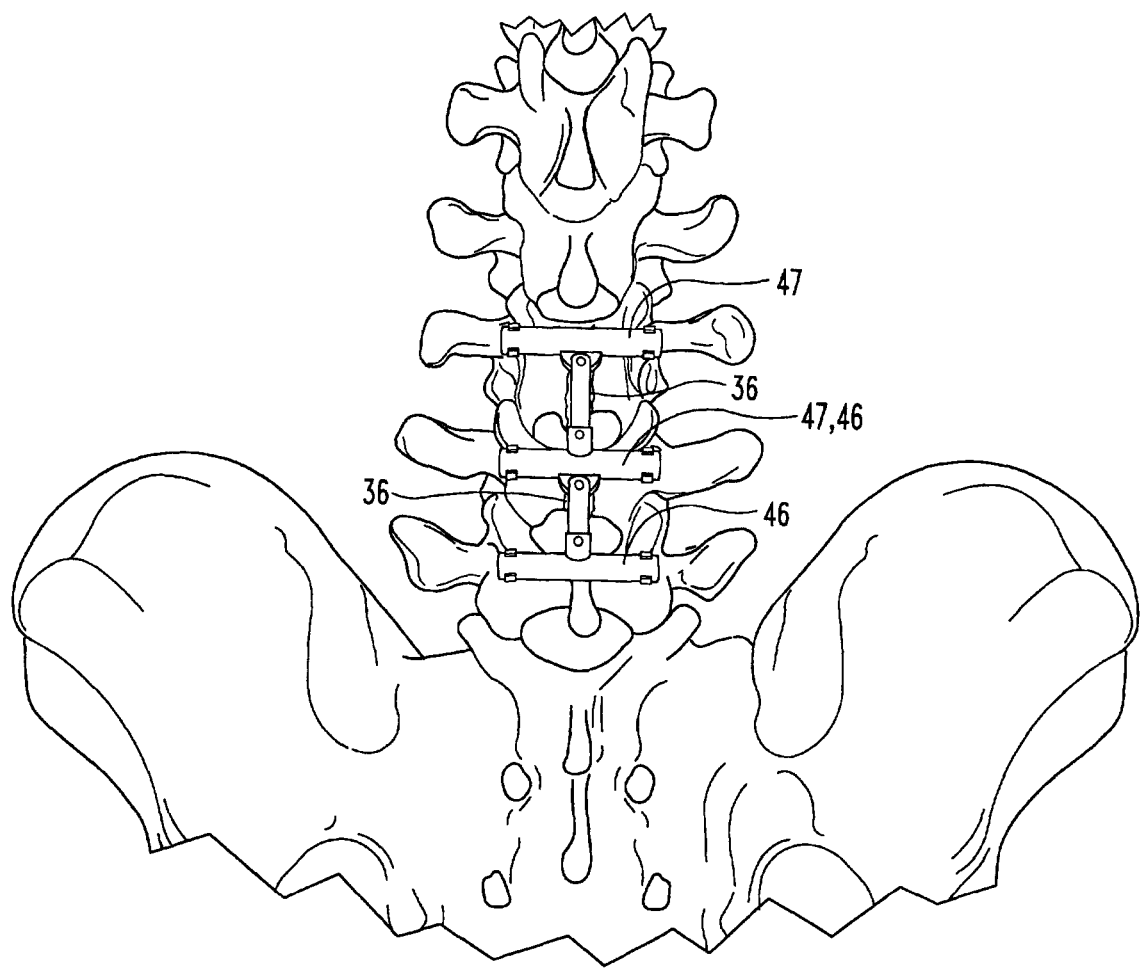
FIG. 4 is a posterior view of the lumbar region of the spine with articulating apparatus according to still another embodiment of the present invention secured thereon.

One advantage of this configuration is that the support rod may protrude less than with typical prior art systems. This is due partly to the fact that the pedicle screws may be angled so the heads of the screws are angled in toward the center of the spine (i.e., a medialized orientation), causing less interference with the back muscles. Also, during the installation of spinal fixation systems, and as shown in FIG. 4, for example, some bone structure may be removed in the center of the vertebrae, which creates a cavity or valley 36. According to the invention, the rod may be recessed within this cavity to further reduce the profile of the device once installed.

Figure 3:
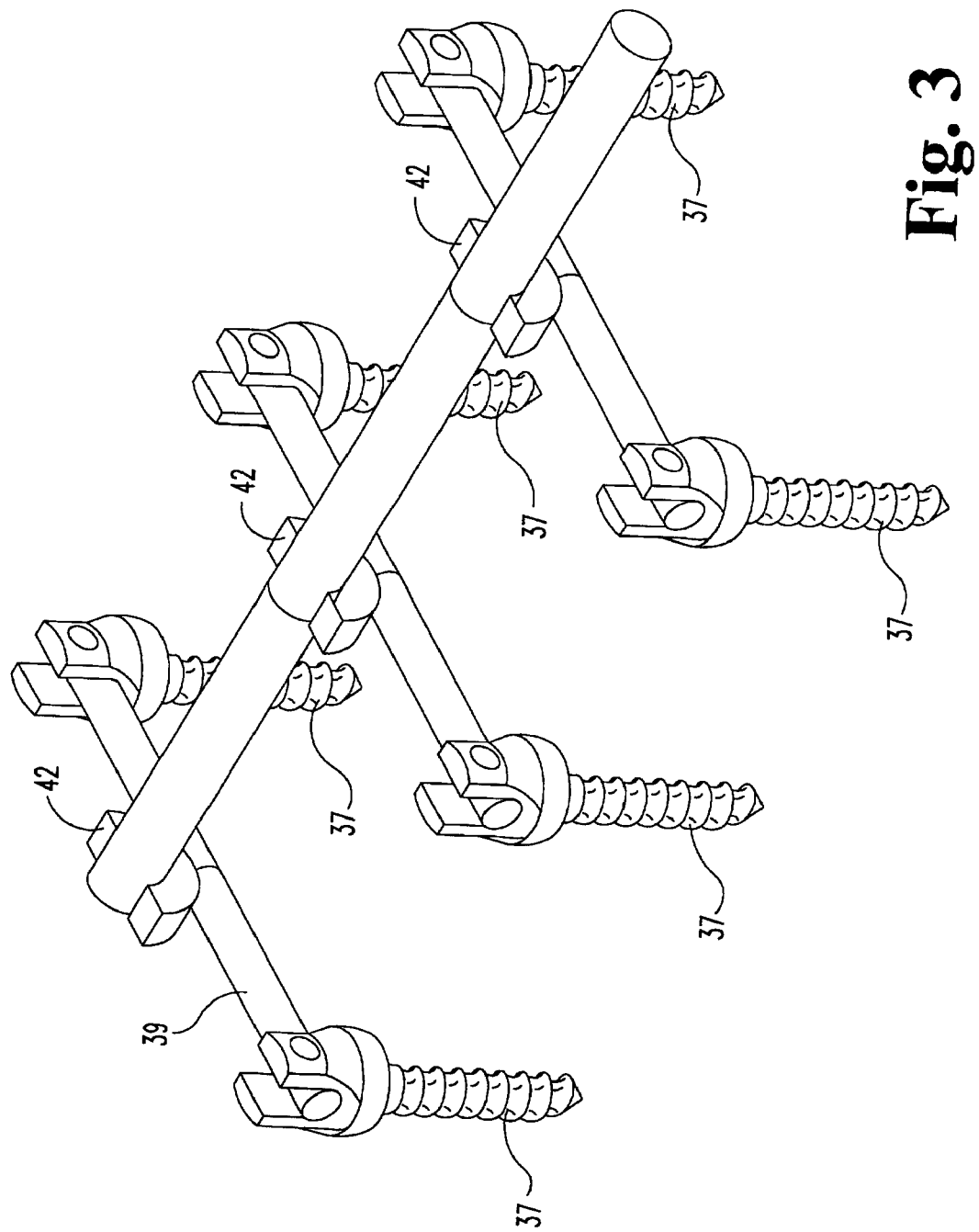
FIG. 3 is a perspective view similar to FIG. 1 but of apparatus according to another embodiment using a different type of pedicle screw and mounting brackets for the support rods.

As mentioned above, poly-axial hinges may be used to attach the pedicle screws to the support rods. More particularly, a pin 27 and locking screw 29 may be used to attach the poly-axial hinge to the screw head, as seen in FIG. 2. In yet another embodiment illustrated in FIG. 3, M-8 type locking pedicle screws 37 as shown in U.S. Pat. No. 6,280,442 and manufactured by the Medtronic Corporation (MSD), for example, may be used with cross-supports 39 extending therebetween. The support rod 41 may be carried by mounting brackets 42 attached to the cross-supports, which may preferably be aligned with the center of the spine. This embodiment may too incorporate the medialized pedicle screw orientation. Of course, those of skill in the art will appreciate that the various embodiments described herein may advantageously use either the current laterally positioned screws or the medialized orientation.

Still other embodiments of the invention may be understood with reference to FIGS. 4-16. These embodiments are directed to articulating spinal fixation systems which may be particularly useful for controlled segmental correction. For example, the centralized articulating system may be used for applications such as deformity of the adult lumbar spine, e.g., scoliosis and possibly for applications toward idiopathic scoliosis, in addition to traditional applications.

The articulating spinal fixation systems illustrated in FIGS. 4-16 may include medialized columns of pedicle screws 37 on either side of the spine, cross rods 46, 47 (FIG. 5) extending between adjacent pedicle screws in each column, and an articulating rod 48 carried by the cross rods. The articulating rod may advantageously provide distraction (FIG. 10) compression (FIG. 11) in the cephalad-caudal plane, rotational correction (FIG. 13) in the coronal plane, and rotational correction in the cross sectional plane (FIG. 12), as will be appreciated by those of skill in the art. For correction of degenerative scoliosis and its associated deformity, correction in all three of these planes may be achieved according to the present invention. The articulating system of the present invention may allow this to occur in the lumbar spine over several segments (FIGS. 4 and 14).

Figure 5:
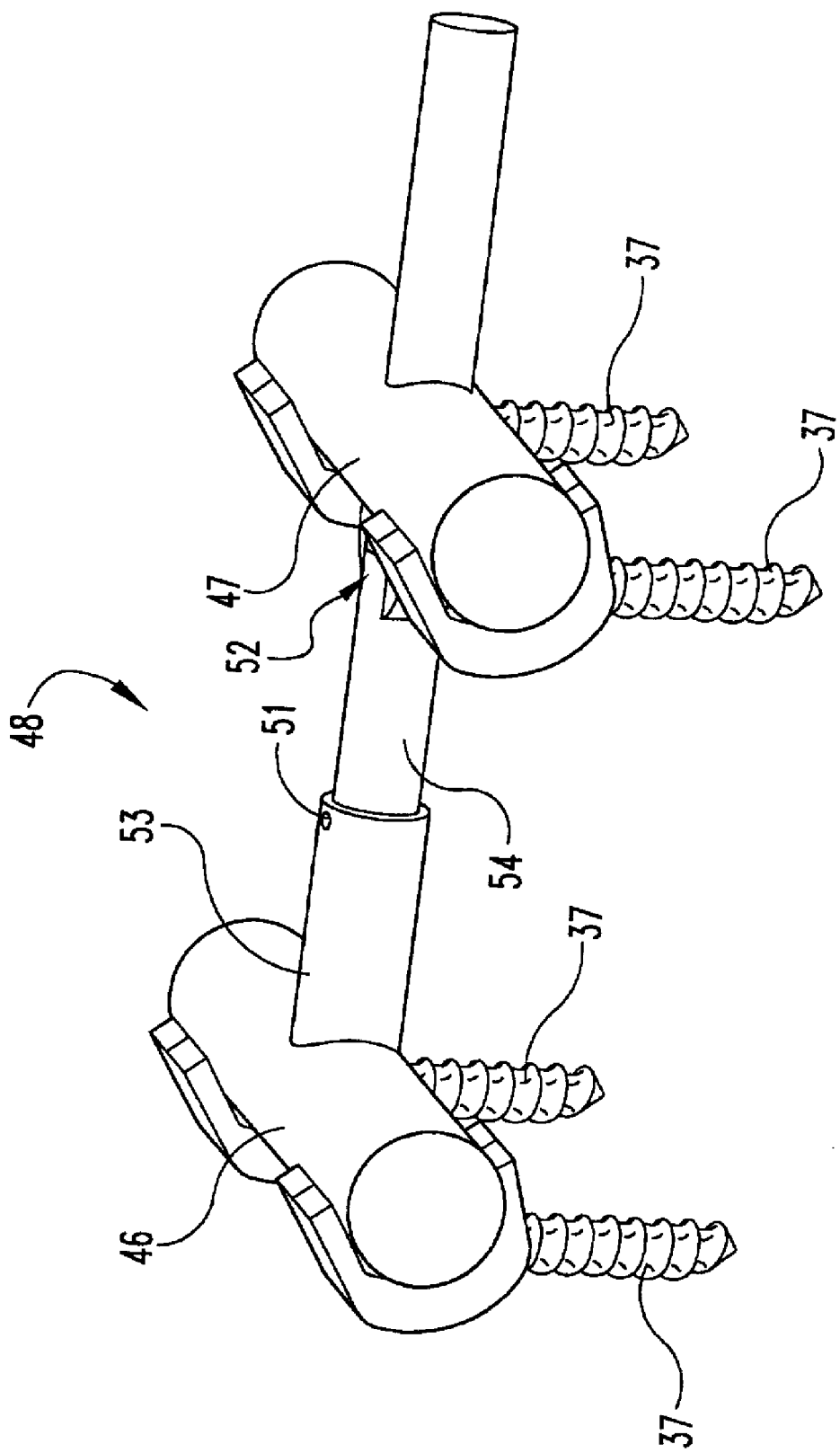
FIG. 5 is an enlarged perspective view of a portion of a typical component used the embodiment of FIG. 4.
Figure 9:
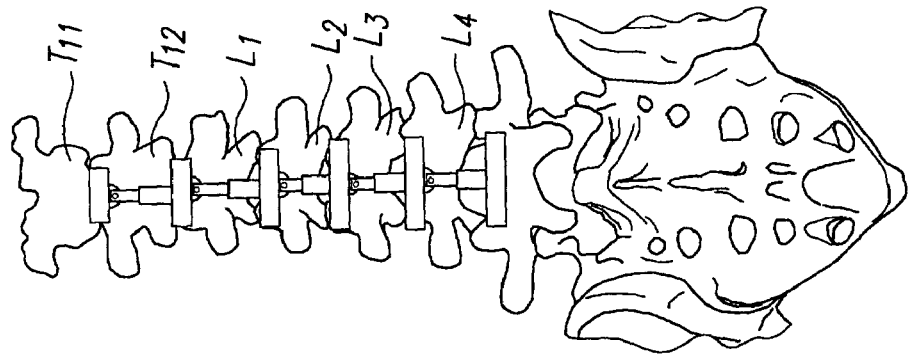
FIG. 9 is a posterior view of the spine following completion of straightening.
Figure 8:
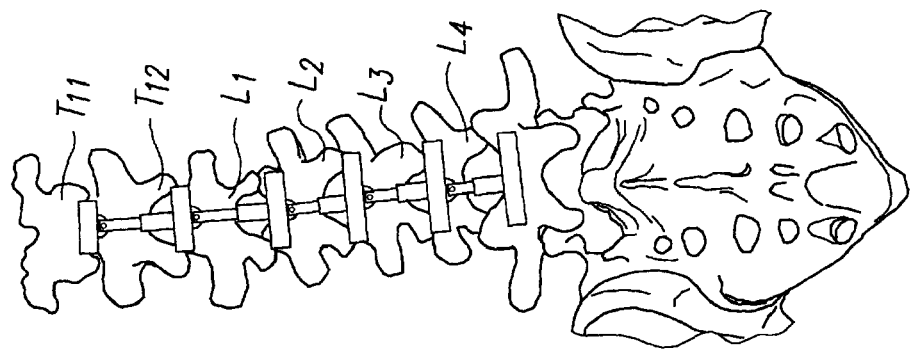
FIG. 8 is a posterior view of the spine ready to complete the straightening.
Figure 7:
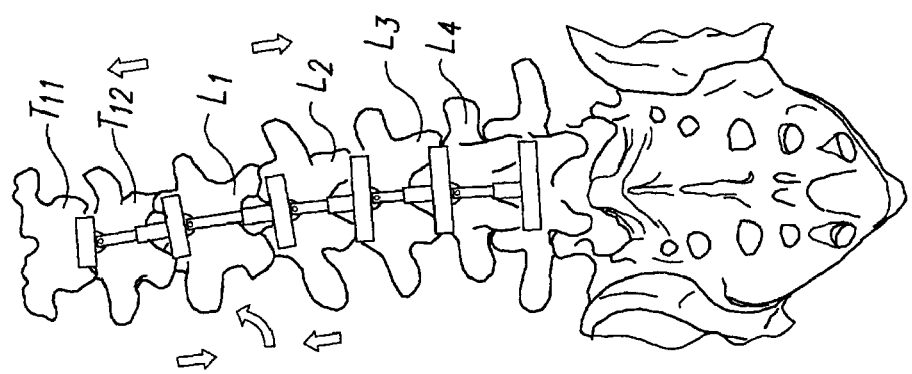
FIG. 7 is a posterior view of the spine of FIG. 6 after using the constructs for rotation.
Figure 6:
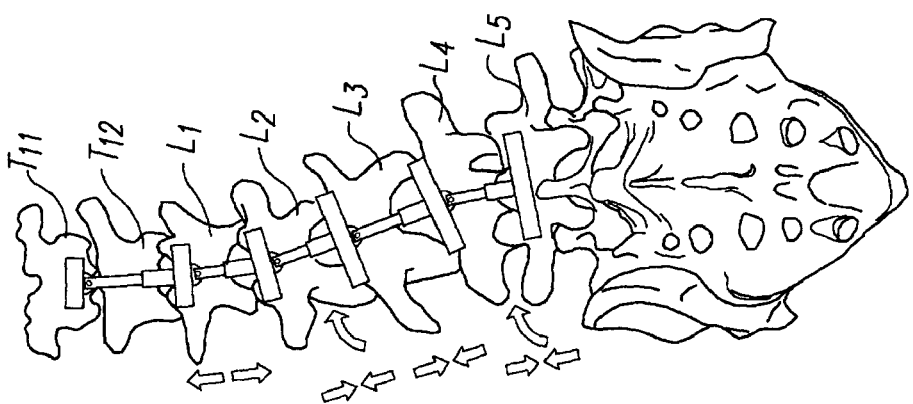
FIG. 6 is a posterior view of a scoliotic spine and employing the instrumentation using the construct of the type shown in FIG. 5.
Figure 11:
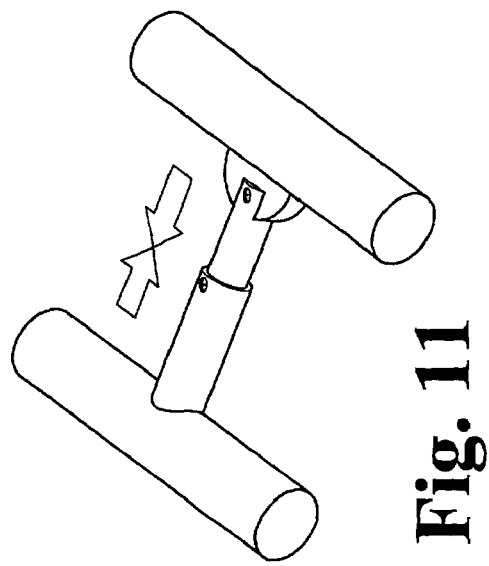
FIG. 11 is a view like FIG. 10 but with the tubing portions retracted as for compression.
Figure 13:
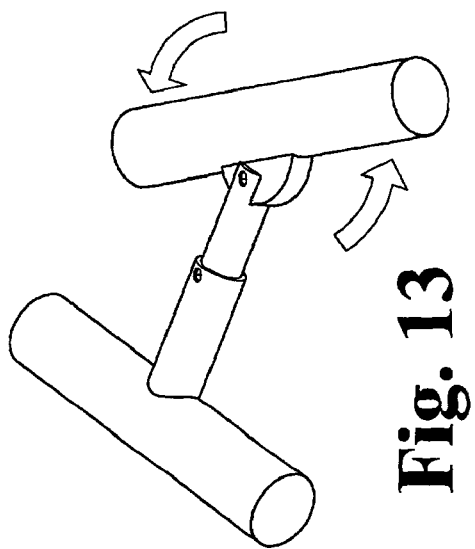
FIG. 13 is an arrangement in which the cross rods are centered at essentially the same distance as in FIG. 12 and co-planar but oriented at converging angles in the same plane.
Figure 10:
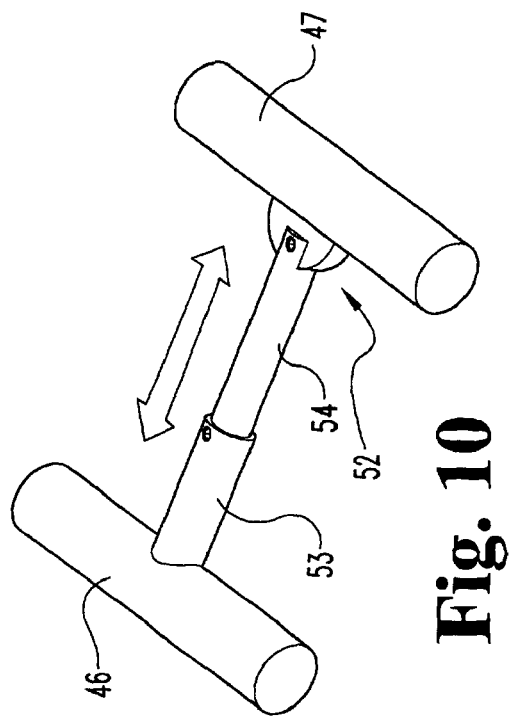
FIG. 10 is a perspective view of the FIG. 5 type of construct with the interfitting telescopic tubing portions of the articulating rod assembly extended to increase spacing between the cross rods (tubes) at an intervertebral location between spinal segments.
Figure 12:
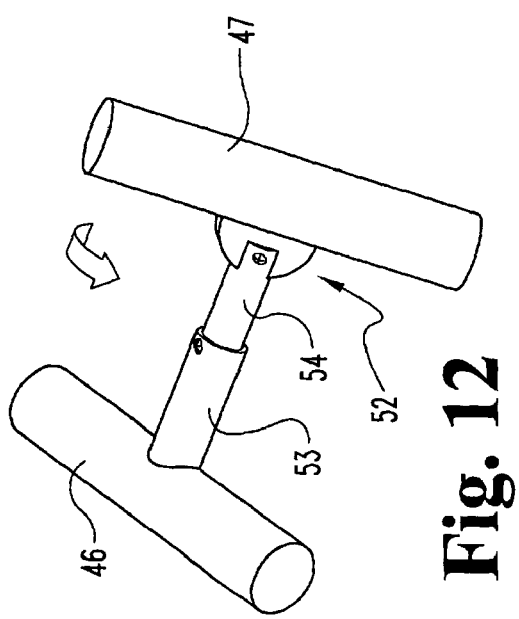
FIG. 12 is an example where the cross rods are at a distance intermediate those of FIGS. 10 and 11 but rotated 90 degrees relative to each other about the colinear axes of the telescoping tubing portions.

A key feature of the articulating system according to the invention is that it provides controlled correction at each segment (FIG. 6). The surgical approach for installing this system may include installing the screws 37 and cross bars with the associated central linking articulating system components of FIG. 5. Then, at each segment (FIG. 6), compression (L4-L5) distraction (L1-L2) rotation (L2-L4) may be performed to facilitate a final controlled segmental correction.

If there were no correction of deformity required, the articulating system could easily be allowed to lock by lock screw 51 (FIGS. 5 and 15), or the illustrated hinge or ball-in-socket mechanisms at 52 may be locked or omitted. A distraction and compression mechanism (telescoping tube portions 53 and 54 with position lock screw 51) of the articulating system may be used to increase intervertebral distance for neural foraminal patency. This is advantageous over dual-rod prior art systems such as those described above in that stresses are applied to all four screws simultaneously, thus decreasing the stress at any one or two of the screws in distraction and compression. This may have a specific benefit in osteoporotic bone.

Figure 14:
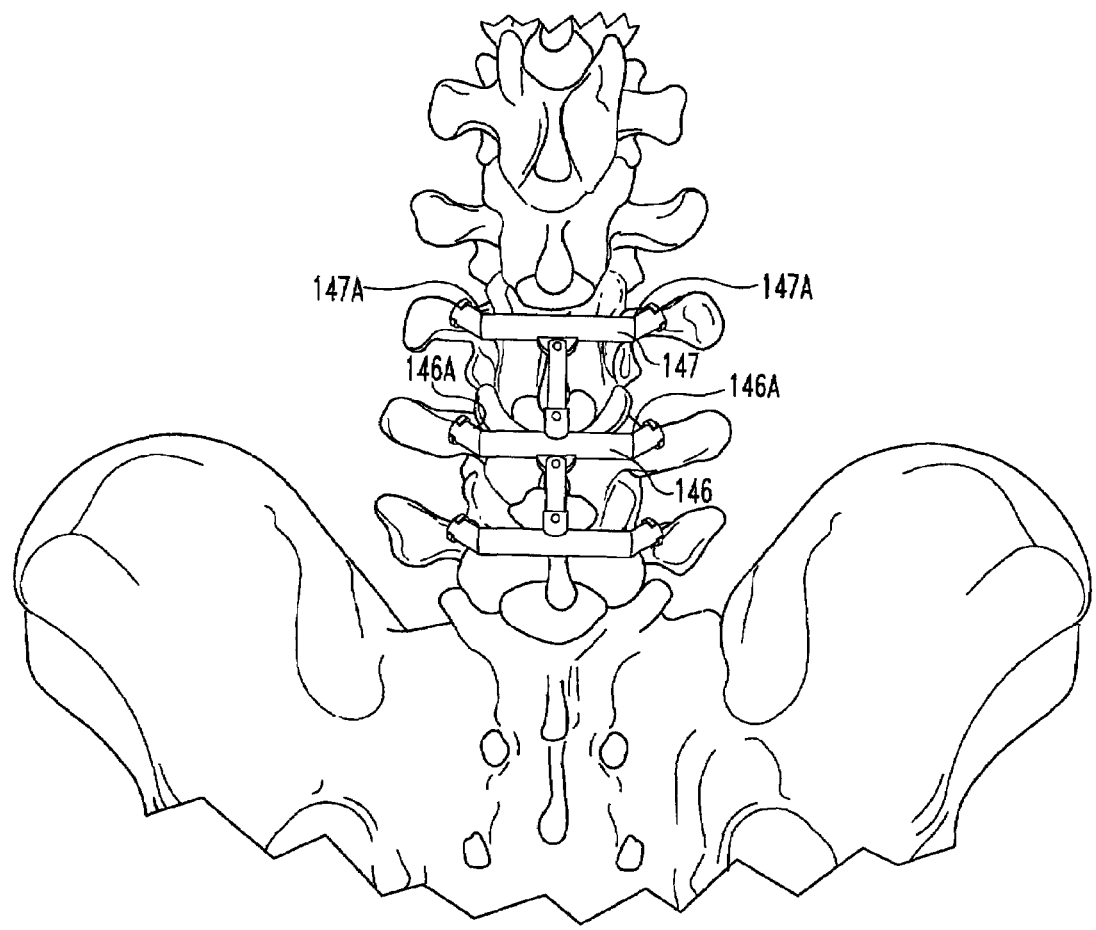
FIG. 14 is a view like FIG. 4 but showing another embodiment wherein the cross rods are formed in an anterior direction near their ends to enable pedicle screw installation from posterior lateral to anterior medial.
Figure 15:
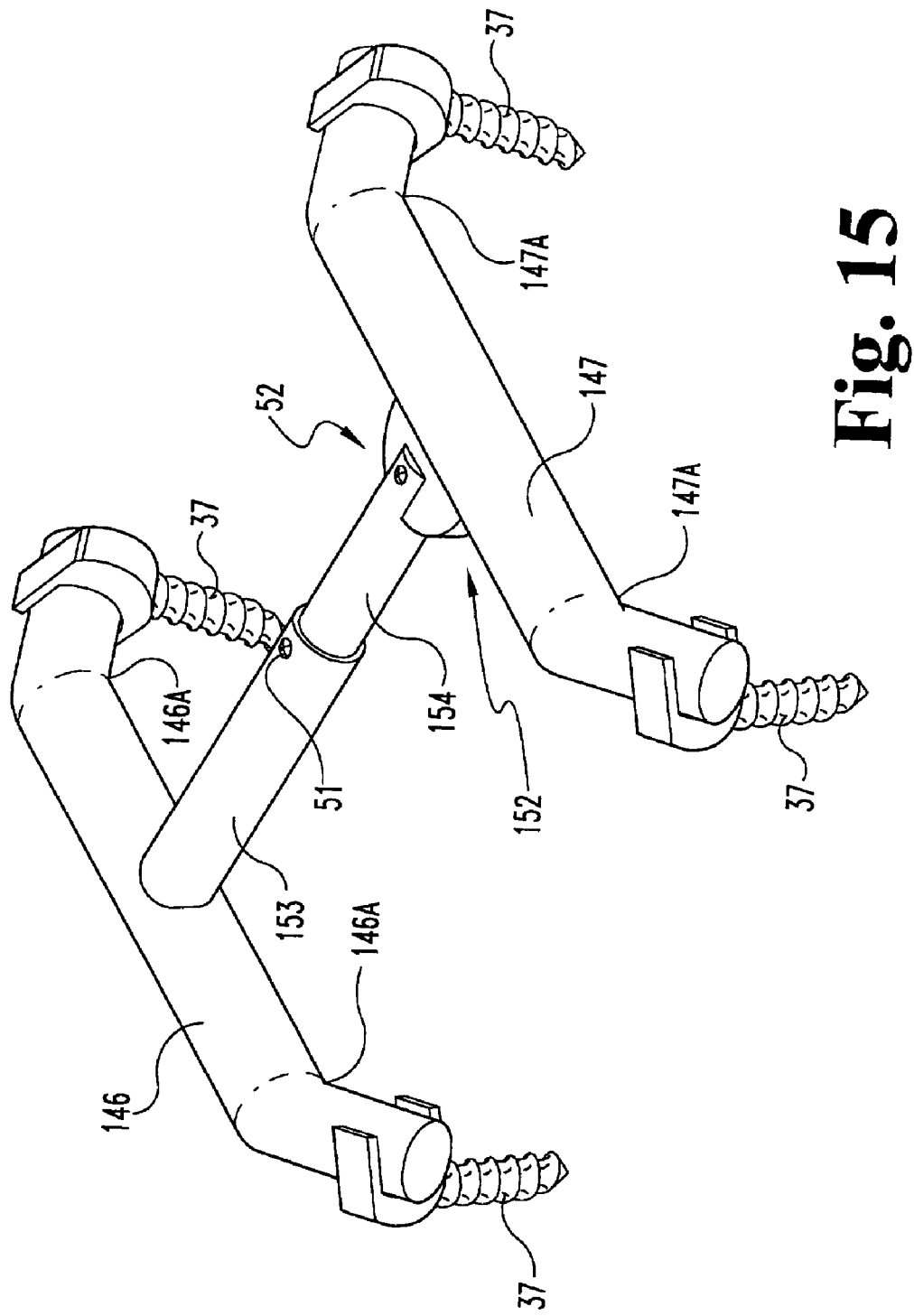
FIG. 15 is an enlarged perspective view of the support construct for the embodiment of FIG. 14.

Again, as shown in FIG. 14 with construct componentry of FIG. 15, the articulating system may advantageously be used with the current lateralized position screws 37 for those surgeons who do not wish to consider a medialized orientation or for special applications which may require such an orientation. For example, for very severe deformities such as Grade III or Grade IV spondylolisthesis, the aberrant anatomy is such that it may be best in these circumstances to either leave the screws higher to cross over the dura or to go to a longitudinal construct.

It will be appreciated by those of skill in the art that the articulating system of the present invention allows surgeons greater control in soft bone for degenerative spines. It may further allow greater capture of the pedicle screws in cortical bone for osteopenic patients with less screw pull out. This may allow greater manipulation of deformity in the elderly spine. This may be particularly difficult with prior art systems because of the weakness of the bone which may cause the pedicle screws to cut through or pull out.

Medial orientation of the pedicle screws may also allow coverage over the muscle to be significantly enhanced. Thus, dissection over the posterolateral recess may not be necessary for lateral grafting with a posterior lumbar interbody fusion (PLIF) approach, especially with the advent of bone morphogenetic protein (BMP). Further, the present invention facilitates the concept of a posterior tension band with anterior column fusion and may also have significant application with regard to absorbable systems, as will be appreciated by those of skill in the art.

Traditional methods for placement of pedicle screw instrumentation in the lumbar and thoracic spine involve identifying bony landmarks and following a trajectory from posterior lateral to anterior medial, as will be understood by those of skill in the art. A method aspect of the present invention is directed to a method which starts more medially and follows a lateral trajectory for pedicle screw insertion (i.e., posterior medial to anterior lateral). The method of present invention provides several advantages over prior art methods. For example, narrower exposure may be required. That is, traditional methods call for dissection to the tips of the transverse process. This may result in a wide band of muscle that is stripped from the bone, de-innervated, and potentially experiences compromised blood supply. By only exposing to the facet joints, this limitation may be dramatically reduced.

Yet another advantage is that the implant mass may be moved to the midline. Medialized instrumentation places the bulk of the mass more toward the midline where massive structures (like the spinous process) are typically found anyway. This permits the muscles to reapproximate naturally back into position once the instrumentation is placed. Additionally, improved biomechanical control and correction of spinal deformity is facilitated.

Traditionally, lateral positioned pedicle screws have been utilized historically for the past 15 or 20 years. The positioning of the screw involves a starting point at the midportion of the transverse process at the lateral wall midportion of the superior facet. The trajectory really begins anywhere from 30 to 40 degrees lateral to a medial position and in the pedicle, transversing toward the midline of the vertebral body along the cephalad border. This progresses up to the lumbar spine to about a 20 degree position or so at the higher lumbar levels.

The method of medialized pedicle screw instrumentation according to the present invention may improve surgical outcome in the use of instrumentation for patients undergoing lumbar stabilization procedures, for example. It has been identified that the dorsal cortex of the transverse process is a critical area of maintenance of bony structure to facilitate holding of the pedicle screw laterally.

The medialized approach of the present invention involves entering the bony construct from the medial inferior portion on the facet, rather than a lateral position. That is, it involves a different trajectory than with prior art systems. Advantages of this method may include ease of insertion, harder and more abundant cortical bone for fixation of screws, smaller screw sizes, potentially less metal in the spine, more favorable trajectory from medial to lateral to reduce the potential for injury of the neural structures, better muscle coverage, easy metal removal and better muscle physiology.

According to the present invention, a laminectomy dissection may be required, i.e., not a typical lateral dissection for posterolateral screw placement, for example. This facilitates reduced stripping of the paravertebral muscles from the transverse processes and reduced denervation of paravertebral muscles. It has been noted in the past that a typical laminectomy incision is less painful and less debilitating than a typical exposure for a lumbar posterolateral fusion. This represents a marked advantage for patient outcome, recovery and postoperative healing.

An initial starting point is identified at the cephalad border of the pars interarticularis at the junction of the caudal aspect of the inferior facet. Along the pars interarticularis at the cephalad border approximately at the perpendicular midportion of transverse process, the pedicle may be identified. This may be visualized after laminectomy, especially from the medial position. The egressing nerve roots beneath the pedicle from cephalad to an inferolateral direction may easily be identified along with the pedicle cortical medial wall.

Two points of entry are possible, for example. Through standard laminectomy the inferomedial portion of the inferior facet may be removed to prevent any abutment against the screw. This does not necessarily involve any more removal of facet than is done with a typical laminectomy. Using a drill, a small starting point may be made in the cortical bone with the direction approximately neutral to 10 degrees medial and the drill may be directed approximately 10 degrees cephalad. The uppermost screw position may be directed more cephalad based on the preoperative CT scan after approximating the angle of the vertebral body endplate compared to the perpendicular.

Using the drill lightly, a small opening may be made in the cortical bone drilling in the appropriate trajectory. Next, appropriate, sharp bone taps may be used because of the greater content of cortical bone in this region. Forces are preferably directed away from the cauda equina in the trajectory. To avoid any facet impingement, by starting the entry, slight caudal pointing to the above starting point at the cephalad border of the pars interarticularis and then angling in the cephalad direction approximately 20 degrees may be performed. This may create a cephalad angulation of the screw and thereby alleviate abutment of the inferior articulating facet.

The lower levels to be included in the fusion need not be of concern, since these facet joints may be included in the fusion mass itself. By way of example, 5.5 mm and 6.5 mm screws can fit in this trajectory fairly well. With anterior column support, such as allograft or cage, smaller size screws may be used, such as 4.0 or 4.5 mm, for example. Of course, other screw sizes may also be used in accordance with the present invention. Generally, the smaller the screw size, the easier the insertion and the greater the range for placement of the screw.

Because of the above trajectory and because of the significant increased amount of cortical bone, the typical 40 to 45 mm length screws used for lateral position may not be required. For example, it has been found that 25 mm screws facilitate excellent hold in this position because of the increased cortical bone. Yet, screws longer than 25 to 30 millimeters are not preferred for secondary to possible lateral exit or penetration of the vertebral body margin. Bicortical purchase, of course, is an option of the surgeon and certainly can be accomplished with careful technique, as will be appreciated by those of skill in the art.

Once the pedicle screws are positioned bilaterally, it is noted that the articulating heads of the M-8 system, for example, may be more centralized and approximate the area of the spinous process rather than lateral to the facet obstructing the paravertebral muscles. This facilitates greater ease of instrumentation. The surgeon may not be required to pull the paravertebral muscles laterally trying to access a lateral starting point. In patients with very deep spine dissections, this may facilitate a much greater ease of the instrumentation because the instrumentation is placed centrally and the surgeon can work from one side of the table.

The rods may be placed in the usual fashion with a typical medialized approach or a central construct system. The central mass of metal is now in a natural physiologic position (spinous process mass) thereby being recognized as a normal physiologic position to the paravertebral muscles. Next, the rods may be placed from cephalad to caudad or transversely based on a new concept of the central construct system.

Cross rods or links may also be utilized in a more rigid fashion with an inverted "V" relationship of the screws to the spine. Once again, the mass of metal may remain centralized. The paravertebral muscle may easily reapproximate with a low profile system, such as that of the present invention. There is a normal physiological position over the facet with the ease of closure of the wound. Normal tension of the paravertebral muscles may be recreated, which is not possible with a lateral position screw system.

Furthermore, there may be less "dead space" for wound healing beneath the spinal fixation systems of the present invention compared to a lateral construct. Again, this facilitates less postoperative drainage, seroma and other possible complications of hematoma. The initial recovery is facilitated to a significant degree due to the method and systems of the present invention. The above method may be used in conjunction with the PLIF technique with anterior construct and/or a facet fusion from a medialized approach rather than a posterolateral fusion.

It is believed that there will be a learning curve to developing the appropriate surgical technique to facilitate the above methods, and it is recommended appropriate instruction be done with cadaveric work before instrumentation with patients. This method for medialized pedicle instrumentation according to the present invention differs from the classic lateral position screw technique in that:

1. Paravertebral muscle mass stripping may not be required which results in much less dissection and thus reduces denervation of the paravertebral muscles, facilitating postoperative recovery and closure of the wound;
2. In deep spine patients with difficult exposure, the medial approach allows ease of placement of instrumentation with forces directed away from the neural elements, thus reducing neurological injury;
3. Placement in significant cortical bone facilitates greater control and deformity correction in osteoporotic and elderly spinal patients with degenerative spondylosis;
4. In thin patients with very poor coverage of hardware, medialization of the hardware allows better coverage than posterolateral screw positioning; and
5. Removal of hardware (which may need to be done for various surgical reasons) is facilitated by the medial approach because the rods and screws are all centralized. Thus, much less dissection is required in the removal of the instrumentation of the present invention than in typical prior art lateral spinal fixation systems.

If the surgeon elects to continue with posterolateral intertransverse process fusion, the medial approach allows for significant exposure of the posterior bony areas for fusion compared to the typical lateral constructs. The medialized approach potentially represents a marked advantage and improvement over the standard technique of lateral positioning for the care of patients with lumbar disorders and facilitates minimal access to the clinical surgical approach to the lumbar spine. The construct of FIGS. 14 and 15 facilitates this, and in this case, the end portions of the cross bars 146 and 147 are provided with a slight posterior to anterior orientation as at location 146A and 147A to go around the facets and enable the lateral trajectory of the bone screws 37 from the outside to the inside. So in this embodiment the cross bars are slightly longer from end-to-end than in the FIGS. 4 and 5 embodiment, but the telescoping tube portions 153 and 154 are the same and can use a swivel of the pin-type 52 or the ball and socket type, located as in the FIGS. 4 and 5 embodiment.

Figure 16:
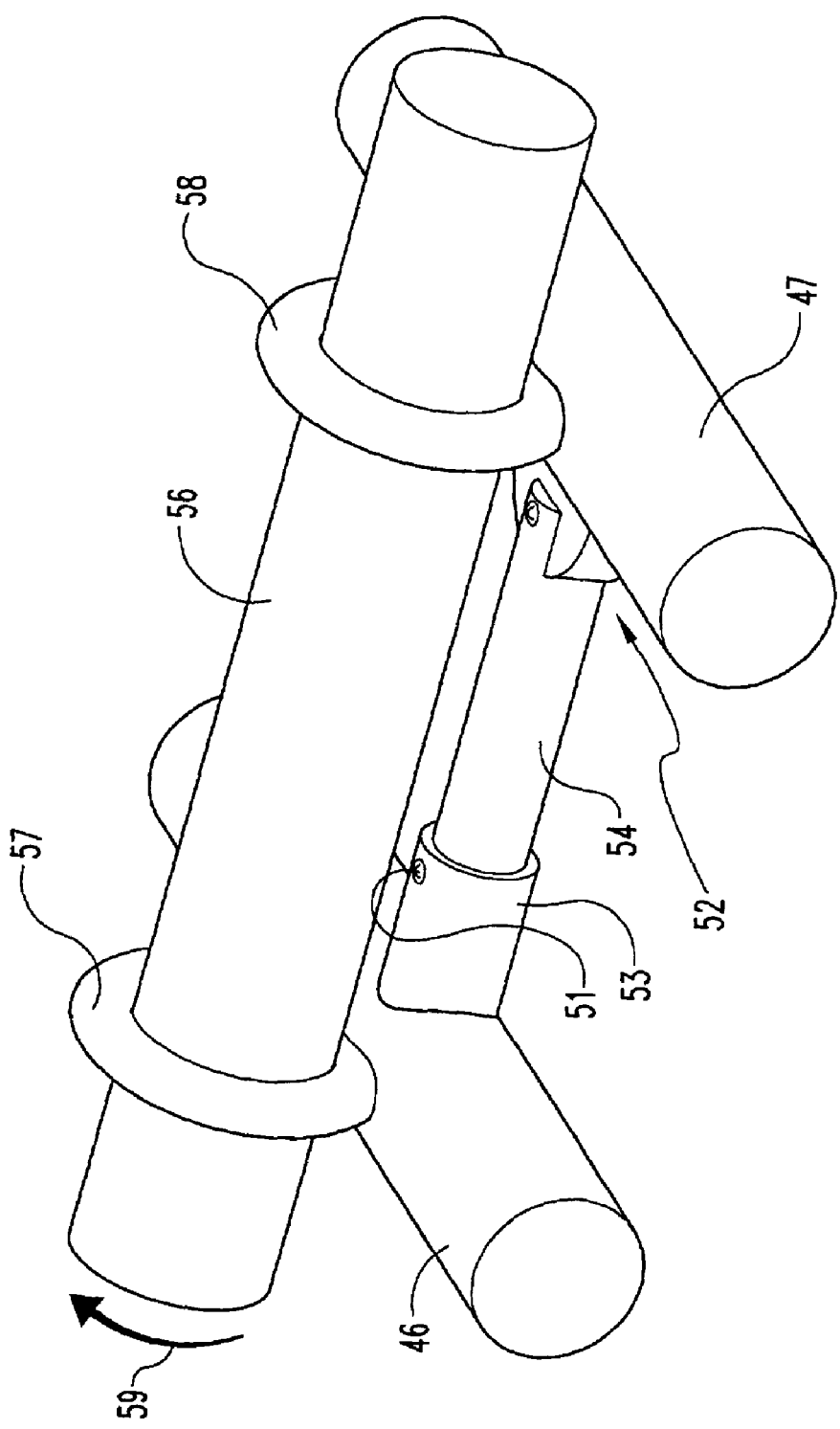
FIG. 16 shows a technique in which the loose, segmented construct of the previous illustrations is supported by a temporary rod during manipulation of the cross rods to correct a deformity.

Referring to FIG. 16 for an example, a loose (locking screws not tight) segmental construct as in FIG. 5, or as in FIG. 15, is placed at a spinal site with the ends of the cross bars attached to the heads of the pedicle screws. A solid rod 56 is temporarily attached to cross rods 46 and 47 with eyebolts 57 and 58. Then the rods 46 and 47 are rotated (arrow 59) relative to each other to correct a deformity. Then locking screws are tightened to tighten the construct. Then the temporary rod 56 and eyebolts 57 and 58 are removed.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that other modifications and embodiments are intended to be included within the scope of the invention as defined by the appended claims, in some of which the term "motion segment" is to be understood as a location in the spine where motion is achieved through a combination of two vertebral bodies with an intervertebral disc in-between.

What is claimed is:

1. A method of instrumentation for patients undergoing spinal treatment and comprising:
   at a first motion segment of the spine, placing a first pedicle screw entering the cephalad border of the pars interarticularis at the junction of the caudal aspect of the inferior facet at one side of the spine;
   at said first motion segment, placing a second pedicle screw entering the cephalad border of the pars interarticularis at the junction of the caudal aspect of the inferior facet at the other side of the spine;
   at a second motion segment of the spine, placing a third pedicle screw entering the cephalad border of the pars interarticularis at the junction of the caudal aspect of the inferior facet at the one side of the spine;
   at the said second motion segment, placing a fourth pedicle screw entering the cephalad border of the pars interarticularis at the junction of the caudal aspect of the interior facet at the other side of the spine;
   connecting a first cross support to the first and second pedicle screws;
   connecting a second cross support to the third and fourth pedicle screws;
   connecting a longitudinal support to said first and second cross supports;
   adjusting the relationship of the cross supports relative to each other;
   and fixing the cross supports to the pedicle screws and to the longitudinal support.

2. The method of claim 1 and comprising:
   adjusting the relationship of the cross supports by changing the distance between the cross supports.

3. The method of claim 1 and comprising:
   adjusting the relationship of the cross supports by changing the angle of the first cross support relative to the second cross support in a plane.

4. The method of claim 1 and comprising:
   adjusting the relationship of the first cross support relative to the second cross support by rotating the first cross support relative to the second cross support about a longitudinal axis of said longitudinal support.

5. The method of claim 1 and comprising:
   prior to connecting said cross supports to said pedicle screws, removing of portions of spinous processes adjacent said motion segments to establish a valley at said motion segments;
   and locating said longitudinal support in said valley.

6. The method of claim 5 and further comprising:
   manipulating the supports in association with the valley at levels of the spinal region associated with said motion segments.

7. The method of claim 6 and further comprising:
   manipulating the supports by rotating one of said cross supports relative to the other cross support about a longitudinal axis of said longitudinal support.

8. The method of claim 6 and further comprising:
   manipulation of the supports by pivoting one of said cross supports relative to said other cross support in a plane containing said other cross support.

9. The method of claim 1, wherein said step of placing a first pedicle screw includes orienting a head of said first pedicle screw in a medialized orientation, and said step of placing a second pedicle screw includes orienting a head of said second pedicle screw in a medialized orientation.

10. The method of claim 9, wherein said step of placing a third pedicle screw includes orienting a head of said third pedicle screw in a medialized orientation, and said step of placing a fourth pedicle screw includes orienting a head of said fourth pedicle screw in a medialized orientation.

11. The method of claim 1, further comprising the step of exposing at least one of said motion segments only to the facet joints.

12. A method of instrumentation for patients undergoing spinal treatment and comprising:
at a first motion segment of the spine, placing a first pedicle screw entering the cephalad border of the pars interarticularis at the junction of the caudal aspect of the inferior facet at one side of the spine;
at said first motion segment, placing a second pedicle screw entering the cephalad border of the pars interarticularis at the junction of the caudal aspect of the inferior facet at the other side of the spine;
at a second motion segment of the spine, placing a third pedicle screw entering the cephalad border of the pars interarticularis at the junction of the caudal aspect of the inferior facet at the one side of the spine;
at the said second motion segment, placing a fourth pedicle screw entering the cephalad border of the pars interarticularis at the junction of the caudal aspect of the interior facet at the other side of the spine;
connecting a first cross support to the first and second pedicle screws;
connecting a second cross support to the third and fourth pedicle screws;
connecting a longitudinal support to said first and second cross supports;
fixing the cross supports to the pedicle screws and to the longitudinal support; and
manipulating the supports by moving telescoping portions of the longitudinal support to provide desired compression and distraction at vertebral bodies associated with said motion segments.

13. The method of claim 12, further comprising making a laminectomy dissection.

14. The method of claim 12, further comprising removal of an inferomedial portion of the inferior facet.

15. The method of claim 12, wherein said manipulating includes rotating a portion of said longitudinal support relative to another portion of said longitudinal support.

16. A method of instrumentation for patients undergoing spinal treatment and comprising:
removing some bone from spinous processes of vertebral bodies adjacent selected motion segments of the spine to provide cavities at the posterior of the spine;
securing a plurality of pairs of pedicle screws in said vertebral bodies, one screw of each pair being in a first column at one side of the spinal foramen, the other screw of each pair being in a second column at the other side of the spinal foramen, said pedicle screws having a trajectory from posterior medial to anterior lateral;
using a plurality of cross supports, each of which cross supports has first and second opposite ends, and connecting said cross supports to said pairs by connecting the first end of each cross support to one screw of one of said pairs, and connecting the second end of said cross support to the other screw of said one pair;
placing in said cavities, a longitudinal support connected to said cross supports;
manipulating said supports to positions to correct relationship of some of said vertebral bodies relative to others of said vertebral bodies; and
locking said supports in said positions.

17. The method of claim 16 and further comprising:
installing said pedicle screws with trajectory from posterior lateral to anterior medial.

18. The method of claim 17 and further comprising:
projecting ends of said cross supports from posterior forward around facets to connect to said pedicle screws.

19. The method of claim 16 and further comprising:
installing said pedicle screws entering the cephalad border of the pars interarticularis at the junction of the caudal aspect of the interior facet, at opposite sides of the spine.

20. The method of claim 16 and wherein:
manipulating said supports includes deforming said longitudinal support.

21. The method of claim 16 and wherein:
manipulating said supports includes swiveling at least one of said cross supports relative to said longitudinal support.

22. The method of claim 21 and wherein:
manipulating said supports includes swiveling more than one of said cross supports relative to said longitudinal support.

23. The method of claim 16 and wherein:
manipulating said supports includes changing the length of said longitudinal support.

24. The method of claim 16, further comprising the step of orienting heads of at least one of the pairs of pedicle screws in a medialized orientation.

25. The method of claim 24, wherein said step of orienting heads includes orienting the heads of at least two of the pairs of pedicle screws in a medialized orientation.

26. The method of claim 16, further comprising the step of exposing at least one of said motion segments only to the facet joints.

27. A method of instrumentation for patients undergoing spinal treatment and comprising:
removing some bone from spinous processes of vertebral bodies adjacent selected motion segments of the spine to provide cavities at the posterior of the spine;
securing a plurality of pairs of pedicle screws in said vertebral bodies, one screw of each pair being in a first column at one side of the spinal foramen, the other screw of each pair being in a second column at the other side of the spinal foramen;
using a plurality of cross supports, each of which cross supports has first and second opposite ends, and connecting said cross supports to said pairs by connecting the first end of each cross support to one screw of one of said pairs, and connecting the second end of said cross support to the other screw of said one pair;
placing in said cavities, a longitudinal support connected to said cross supports;
manipulating said supports to positions to correct relationship of some of said vertebral bodies relative to others of said vertebral bodies; and
locking said supports in said positions;
wherein manipulating said supports includes rotating a portion of said longitudinal support relative to another portion of said longitudinal support.

28. The method of claim 27, further comprising making a laminectomy dissection.

29. The method of claim 27, further comprising removal of an inferomedial portion of the inferior facet.

30. The method of claim 27, wherein said manipulating further includes moving telescoping portions of the longitudinal support to provide desired compression and distraction at vertebral bodies associated with said motion segments.

31. A method of instrumentation for patients undergoing spinal treatment and comprising:
- at a first motion segment of the spine, placing a first pedicle screw having a head, said head of said first pedicle screw being oriented in a medialized orientation;
- at said first motion segment, placing a second pedicle screw having a head, said head of said second pedicle screw being oriented in a medialized orientation;
- at a second motion segment of the spine, placing a third pedicle screw;
- at said second motion segment, placing a fourth pedicle screw, wherein said third and fourth pedicle screws each have a head, said heads of said third and fourth pedicle screws being oriented in a medialized orientation;
- connecting a first cross support to the first and second pedicle screws;
- connecting a second cross support to the third and fourth pedicle screws;
- connecting a longitudinal support to said first and second cross supports; and
- fixing the cross supports to the pedicle screws and to the longitudinal support.

32. The method of claim 31, further comprising the step of adjusting the relationship of the cross supports relative to each other.

33. The method of claim 32, wherein said adjusting step includes at least one of distraction, compression and rotation.

34. A method of instrumentation for patients undergoing spinal treatment and comprising:
- removing bone from spinous processes of vertebral bodies adjacent selected motion segments of the spine;
- securing a plurality of pairs of pedicle screws in said vertebral bodies, one screw of each pair being in a first column, the other screw of each pair being in a second column;
- using a plurality of cross supports, each of which cross supports has first and second opposite ends, and connecting said cross supports to said pairs by connecting the first end of each cross support to one screw of one of said pairs, and connecting the second end of said cross support to the other screw of said one pair;
- placing a longitudinal support connected to said cross supports;
- manipulating at least said longitudinal support to correct a relationship of some of said vertebral bodies relative to at least another of said vertebral bodies, said manipulating including at least one of rotating a portion of said longitudinal support relative to another portion of said longitudinal support and moving telescoping portions of the longitudinal support.

* * * * *